(12) United States Patent
Biggins et al.

(10) Patent No.: US 6,666,555 B2
(45) Date of Patent: Dec. 23, 2003

(54) OPHTHALMIC REFRACTOR HAVING RETROFITTABLE READOUT ILLUMINATION

(75) Inventors: David Biggins, Williamsville, NY (US); Douglas H. Hoover, Corfu, NY (US); Carl E. Hynes, Williamsville, NY (US); Donald E. Miller, West Seneca, NY (US)

(73) Assignee: Reichert, Inc., Depew, NY (US)

( * ) Notice: Subject to any disclaimer, the term of this patent is extended or adjusted under 35 U.S.C. 154(b) by 92 days.

(21) Appl. No.: 10/037,326

(22) Filed: Nov. 9, 2001

(65) Prior Publication Data

US 2003/0090630 A1 May 15, 2003

(51) Int. Cl.⁷ .................................................. A61B 3/02
(52) U.S. Cl. ........................ 351/233; 351/218; 351/235
(58) Field of Search ................................. 351/216, 217, 351/218, 233, 234, 235; 362/23, 29, 30, 84; 116/310, DIG. 35

(56) References Cited

U.S. PATENT DOCUMENTS 5,842,764 A * 12/1998 Berardi ........................ 362/23

* cited by examiner

Primary Examiner—George Manuel
(74) Attorney, Agent, or Firm—Hodgson Russ LLP

(57) ABSTRACT

A subjective ophthalmic refractor is improved for operator visibility in a darkened examination room by forming a cylinder axis scale of the refractor as a light-transmitting component having opaque scale gradations and installing a polar array of illumination sources to project light through the cylinder axis scale, which preferably includes a translucent material for diffuse illumination. In an alternative embodiment, the cylinder axis scale includes a photoluminescent material to which the scale gradations are applied. The refractor is further improved by installing respective illumination sources near a cylinder power readout and a sphere power readout of the refractor. The disclosure additionally relates to a method for retrofitting an ophthalmic refractor to illuminate the cylinder axis scale, cylinder power readout, and sphere power readout.

22 Claims, 4 Drawing Sheets

OPHTHALMIC REFRACTOR HAVING RETROFITTABLE READOUT ILLUMINATION

BACKGROUND OF THE INVENTION

I. Field of the Invention

The present invention relates generally to ophthalmic instruments, and more particularly to subjective ophthalmic refractors for evaluating refractive characteristics of a patient's eye.

II. Description of the Related Art

A subjective ophthalmic refractor typically comprises left-eye and right-eye batteries each having a defined viewing path along which an operator may selectively introduce combinations of testing lenses having known refractive properties. During examination, the patient is positioned in a darkened room with his or her eyes aligned to view a projected target chart along the viewing paths defined by the left-eye and right-eye batteries. The operator then performs well-known refracting procedures, including refraction using astigmatic charts and the Jackson cross-cylinder test. A goal of the examination procedure is to determine the sphere power, cylinder power, and cylinder axis of each eye in order to prescribe a suitable pair of corrective lenses.

In order to assess sphere power, the operator must rotate a strong sphere control knob and a weak sphere dial on the associated refractor battery to position chosen spherical power lenses in series in the viewing path. The numerical diopter value of the resultant sphere power introduced in the viewing path is reported to the operator by a sphere power readout provided on the refractor battery. A rotatable cylinder power control knob enables the operator to adjust the power of a cylinder lens introduced in the viewing path, and a numerical diopter value of the cylinder power is displayed by a cylinder power readout on the refractor battery. The axis orientation of the cylinder lens is controlled by a cylinder axis knob that includes a pair of diametrically opposite cylinder axis pointers. The cylinder axis knob is mounted for rotation relative to a coaxially arranged cylinder axis scale circumferentially surrounding the cylinder axis knob and having angular scale gradations. Typically, the scale gradations are marked in five-degree increments, and two complementary protractor scales of one-hundred eighty degrees surround the cylinder axis knob.

Because the examination room is darkened for purposes of target chart projection, the task of reading the sphere power and cylinder power readouts, and of finding the location of the cylinder axis pointers with respect to the cylinder axis scale, is a difficult one for the operator. During the course of a day in which the operator sees many patients, fatigue becomes a factor and the likelihood of errors in reading the refraction data increases. Operators have been known to use a pocket ophthalmoscope to illuminate the sphere and cylinder power readouts and the cylinder axis scale, however this is not the intended use of an ophthalmoscope.

The R. H. Burton Company of Grove City, Ohio has addressed this problem by providing an ophthalmic refractor wherein the sphere power readout, the cylinder power readout, and the cylinder axis scale are illuminated according to an arrangement described in U.S. Pat. No. 5,281,984. This patent teaches the use of a single light bulb supplying light to a light guide mounted on the refractor battery housing of each refractor battery. The light guide is formed of transparent material and is configured to provide a first transparent output around the periphery of the cylinder axis scale, a second transparent output adjacent to the cylinder power readout, and a third transparent output adjacent to the spherical power readout. While this arrangement solves the problem in a suitable manner, it does have certain drawbacks. For example, when the bulb burns out, illumination is ceased at the sphere power readout, the cylinder power readout, and the cylinder axis scale all at once. Another drawback is that the specially configured light guide is not retrofittable to older refractor models from R. H. Burton Company and to ophthalmic refractors from other manufacturers. Finally, the patent contains no teaching of how to arrange a power supply cord connected to the bulb in a manner that will not interfere with the patient or operator.

BRIEF SUMMARY OF THE INVENTION

Therefore, it is an object of the present invention to provide an ophthalmic refractor with means for illuminating a sphere power readout, a cylinder power readout, and a cylinder axis scale of the refractor such that they may be readily and clearly viewed by an operator in a darkened examination room.

It is another object of the present invention to provide an ophthalmic refractor with means for independently illuminating a sphere power readout, a cylinder power readout, and a cylinder axis scale of the refractor such that an illumination source failure with respect to one of these elements does not affect illumination of the other elements.

It is a further object of the present invention to provide an ophthalmic refractor with means for connecting a power source to various illumination sources thereof such that power cords or the like are unobtrusive to the patient and operator.

It is a further object of the present invention to provide an ophthalmic refractor with means for illuminating a sphere power readout, a cylinder power readout, and a cylinder axis scale of the refractor that is retrofittable to a wide range of ophthalmic refractor models.

It is a further object of the present invention to provide a method of retrofitting an ophthalmic refractor with means for illuminating a sphere power readout, a cylinder power readout, and a cylinder axis scale of the refractor.

The present invention involves improvement of a subjective ophthalmic refractor of the type comprising left-eye and right-eye batteries, a mounting bracket for pivotally suspending the left-eye and right-eye batteries from a stand, each battery having a patient viewing path, a strong sphere control knob for selectively positioning a strong sphere lens of chosen power in the patient viewing path, a weak sphere control dial for selectively positioning a weak sphere lens of chosen power in the patient viewing path, a sphere power readout for displaying the cumulative power of the chosen strong and weak sphere lenses to an operator, a cylinder power knob for selectively positioning one or more cylinder lenses of chosen power in the patient viewing path, a cylinder power readout corresponding to the cylinder power knob for displaying the resultant power of the cylinder lenses to an operator, a polar cylinder axis scale, and a cylinder axis knob coaxial with and rotatable relative to the cylinder axis scale for adjusting the cylinder axis of the cylinder lenses, wherein the cylinder axis knob includes at least one cylinder axis pointer cooperating with the cylinder axis scale for indicating the cylinder axis to an operator. An ophthalmic refractor of the above-mentioned type is improved by forming the cylinder axis scale as a light-transmitting component having opaque scale gradations, and installing a polar array of illumination sources arranged to project light through the cylinder axis scale. The cylinder axis scale preferably includes a translucent material for diffuse illumination. In an alternative embodiment, the cylinder axis scale simply includes a photoluminescent material having scale gradations applied thereto. To enhance the visibility of the cylinder axis pointers with respect to the cylinder axis scale, the cylinder axis pointers are preferably formed as light-transmitting areas on the cylinder axis knob that overlap with the cylinder axis scale, or the pointers are opaque markings on an annular translucent flange overlapping with the cylinder axis scale.

The ophthalmic refractor is further improved by installing a cylinder power illumination source near the cylinder power readout, and by installing a sphere power illumination source near the sphere power readout.

In a preferred embodiment of the invention, the light sources are light-emitting diodes connected to a power source via a slip ring arranged to conduct electricity through the pivotal connection between the mounting bracket and the remainder of the refractor, whereby external power cords in the region of the patient or the operator can be avoided.

The invention further encompasses a method for retrofitting an ophthalmic refractor of the above-mentioned type. The method comprises the steps of removing the cylinder axis knob and cylinder axis scale from each battery housing, opening each battery housing, fixing a polar array of illumination sources within each battery housing, arranging power lines leading to each polar array of illumination sources for enabling a power source to be connected the arrays, closing each battery housing, and installing a replacement cylinder axis scale over each polar array of illumination sources, the replacement cylinder axis scale being formed as a light-transmitting component having opaque scale gradations, and mounting either the original cylinder axis knob or a replacement cylinder axis knob to be coaxial with the replacement cylinder axis scale. Where the original cylinder axis knob is reused, machining a cut-out area in place of a cylinder axis pointer on the cylinder axis knob is a preferred additional retrofit step. The method preferably comprises the further steps of installing a cylinder power illumination source in each battery housing proximate the respective cylinder power readout, and installing a sphere power illumination source in each battery housing proximate the respective sphere power readout.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DETAILED DESCRIPTION OF THE INVENTION

Figures 1, 2:
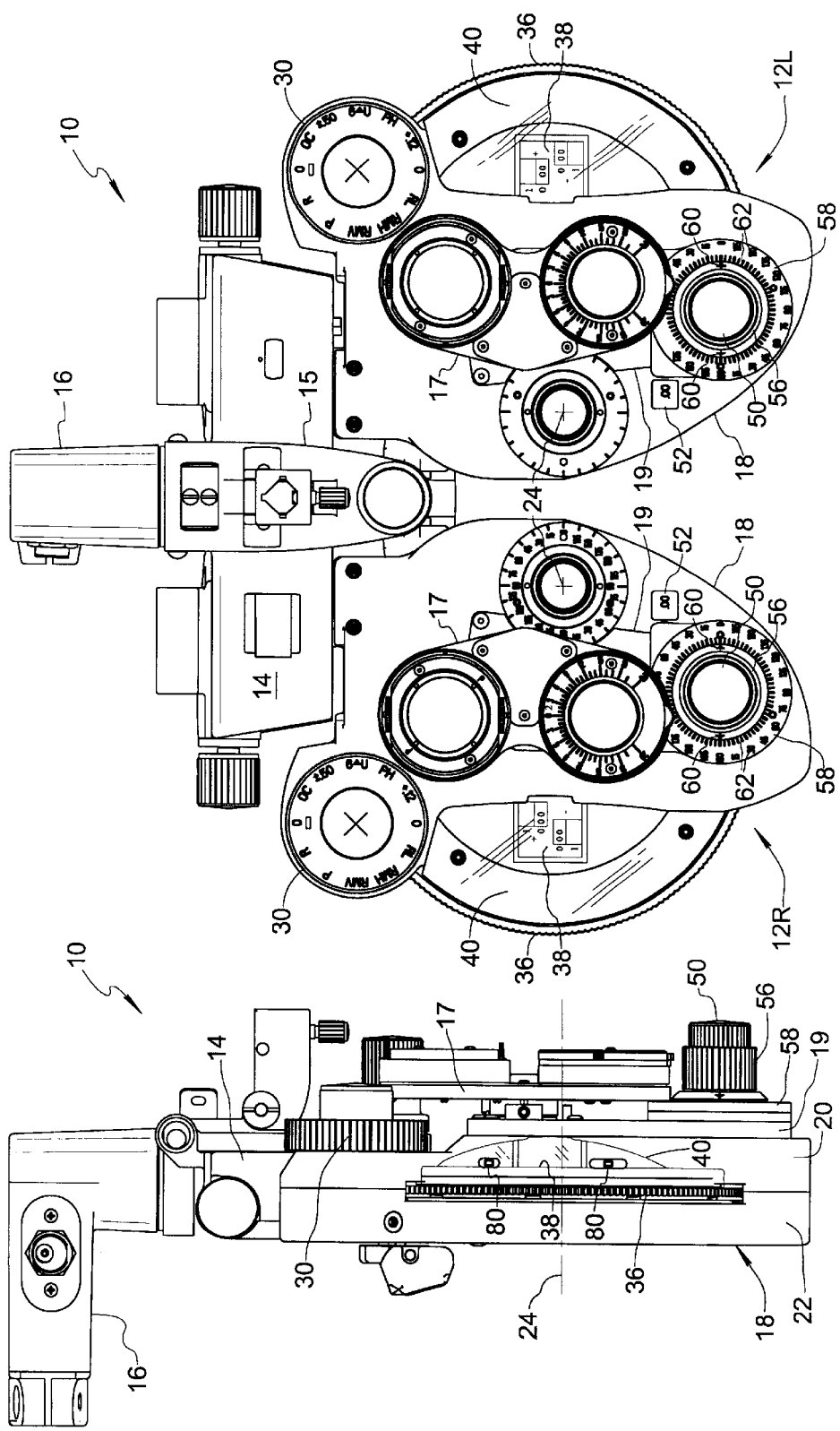
FIG. 1 is a front elevational view of an ophthalmic refractor formed in accordance with a preferred embodiment of the present invention.
FIG. 2 is a side elevational view thereof.

Reference is directed initially to FIGS. 1 and 2 of the drawings showing an ophthalmic refractor 10 having a left-eye battery 12L and a right-eye battery 12R. Batteries 12L and 12R depend from an upper slider track 14 held by a central support 15 of refractor 10 to allow for adjustment of interpupillary distance to fit the patient. Central support 15 is pivotally connected to a mounting bracket 16, whereby the refractor 10 can be supported on a stand (not shown) and positioned in front of the face of a patient. Right-eye battery 12R will now be described in further detail, it being understood that left-eye batter 12L is a mirror image of the right-eye battery.

Right-eye battery 12R includes a housing 18 comprising a front half-shell 20 and a rear half-shell 22, and a viewing path 24 through the housing. Referring also now to the sectional view of FIG. 6, it can be seen that housing 18 encloses a strong sphere lens disc 26 carrying a plurality of strong sphere lenses 28 each having a different optical power. For example, strong sphere lens disc 26 preferably includes a polar array of twelve sphere lenses (including a zero-power opening) differing in power by steps of three diopters, and is rotatable by means of a strong sphere control knob 30 operatively connected thereto for enabling an operator to position a chosen strong sphere lens in viewing path 24. Housing 18 also encloses a weak sphere lens disc 32 having a plurality of weak sphere lenses 34 each having a different optical power. For example, weak sphere lens disc 32 preferably includes a polar array of twelve sphere lenses (including a zero-power opening) differing in power by steps of one-quarter diopter, and is rotatable by means of a weak sphere dial 36 to allow the operator to position a chosen weak sphere lens in viewing path 24. The chosen strong sphere lens 28 and weak sphere lens 34 combine in an additive manner to provide a resultant refracting sphere power along viewing path 24. In the ULTRAMATIC® RX MASTER PHOROPTOR® refracting instrument manufactured by Reichert Ophthalmic Instruments, a division of Leica Microsystems Inc. (assignee of the present application), the resultant sphere power can be adjusted through a range from −19.00 diopters through +16.75 diopters in quarter diopter increments. The numerical diopter value of the resultant sphere power is displayed at a sphere power readout 38 visible through a transparent cover portion 40 of housing 18.

Housing 18 further encloses a strong cylinder lens carrier 42 comprising an array of strong cylinder lenses 44 (including a zero-power opening), and a weak cylinder lens carrier 46 comprising an array of weak cylinder lenses 48 (including zero-power openings). Cylinder lens carriers 42 and 46 are rotatably mounted within housing 18, and cylinder lenses 44 and 48 are specified according to a graded series of cylinder power. The rotational positions of cylinder lens carriers 42 and 46 are controlled in tandem by rotating a cylinder power knob 50 operatively linked to cylinder lens discs 42 and 44, whereby different combinations of a strong cylinder lens 44 and a weak cylinder lens 48 are positionable in viewing path 24. By way of example, in the PHOROPTOR® refracting instrument mentioned above, the resultant cylinder power can be adjusted through a range from 0.00 diopters through 6.00 diopters in quarter diopter increments. The numerical diopter value of the resultant cylinder power is displayed at a cylinder power readout 52 through housing 18 near cylinder power knob 50.

The strong cylinder lenses 44 and weak cylinder lenses 48 are mounted in their respective carriers 42 and 46 by lens holders 54 that enable rotation of each cylinder lens relative to the carrier about an axis of the lens, thereby allowing for adjustment of the cylinder axis orientation. When a selected strong cylinder lens 44 and weak cylinder lens 48 are aligned in viewing path 24, a cylinder axis knob 56 is operatively linked to lens holders 54 such that rotation of cylinder axis knob 56 causes a corresponding rotation of the lens holders 54 and the associated strong and weak cylinder lenses for adjustment of the cylinder axis. A polar cylinder axis scale 58 is fixedly mounted on housing 18, and more particularly on a turret island 19 of housing 18, in coaxial surrounding relation to cylinder axis knob 56, which includes a pair of diametrically opposite cylinder axis pointers 60 pointing to angular gradations indicated on cylinder axis scale 58. Once again by way of example, the cylinder axis scale of the PHOROPTOR® refracting instrument provides two complementary 180° protractor scales having angular values indicated at five-degree intervals. Thus, the operator rotates cylinder axis knob 56 to adjust the angular orientation of the cylinder axis, and this orientation is indicated by the location of cylinder axis pointers 60 with respect to cylinder axis scale 58.

To this point in the detailed description, the elements of ophthalmic refractor 10 are well-known as prior art and are generally familiar to ophthalmic practitioners. The present invention departs from the prior art, and represents an improvement in ophthalmic refractors of the type described above, with respect to illumination of the cylinder axis scale 58, the cylinder power readout 52, and the sphere power readout 38 of ophthalmic refractor 10.

Figure 5:
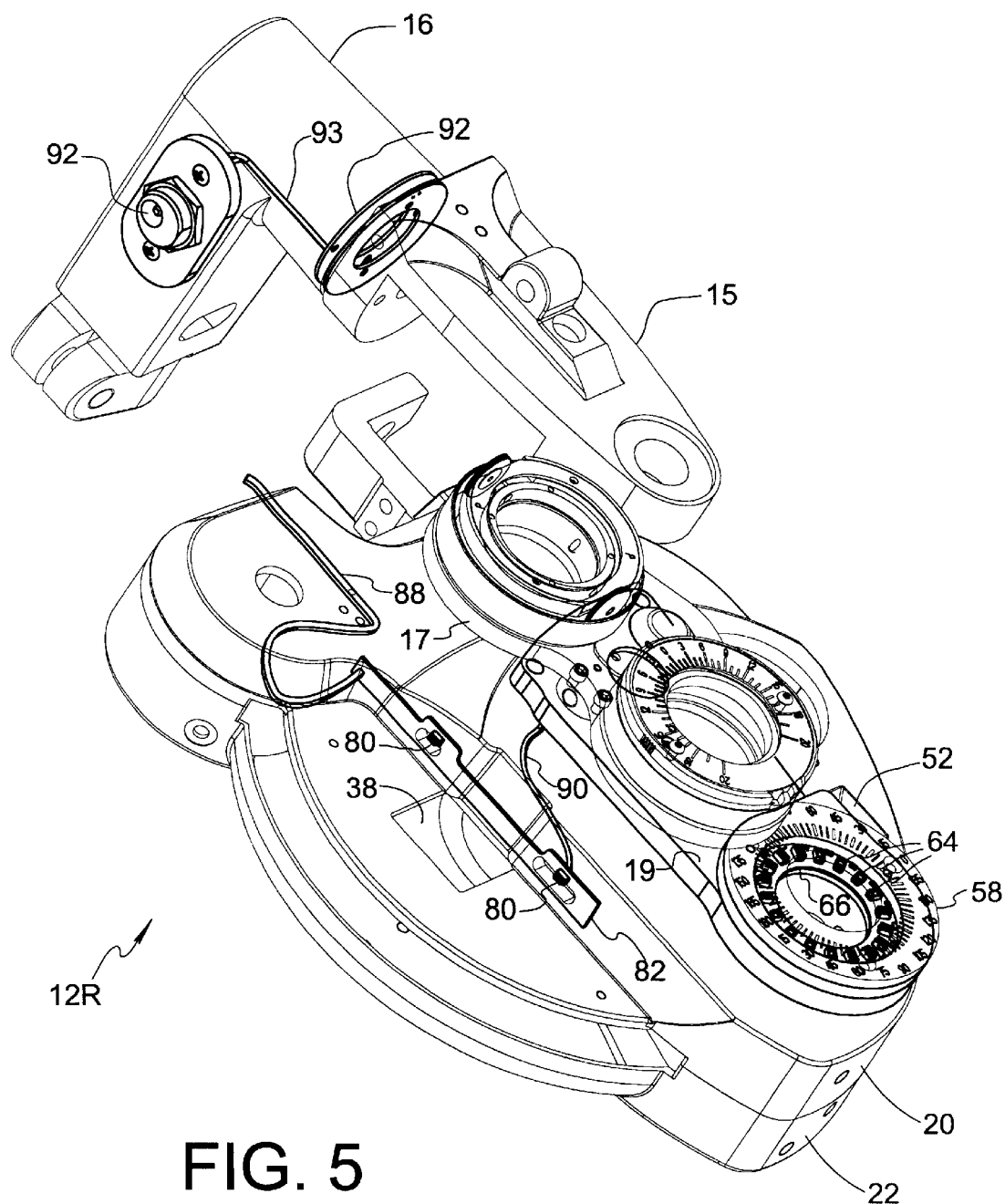
FIG. 5 is a transparent perspective view of the right eye battery shown in FIG. 3, with knobs removed for sake of clarity.
Figure 7:
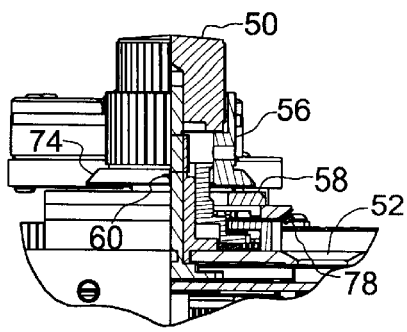
FIG. 7 is a view taken generally along the section line II—II in FIG. 4.
Figure 6:
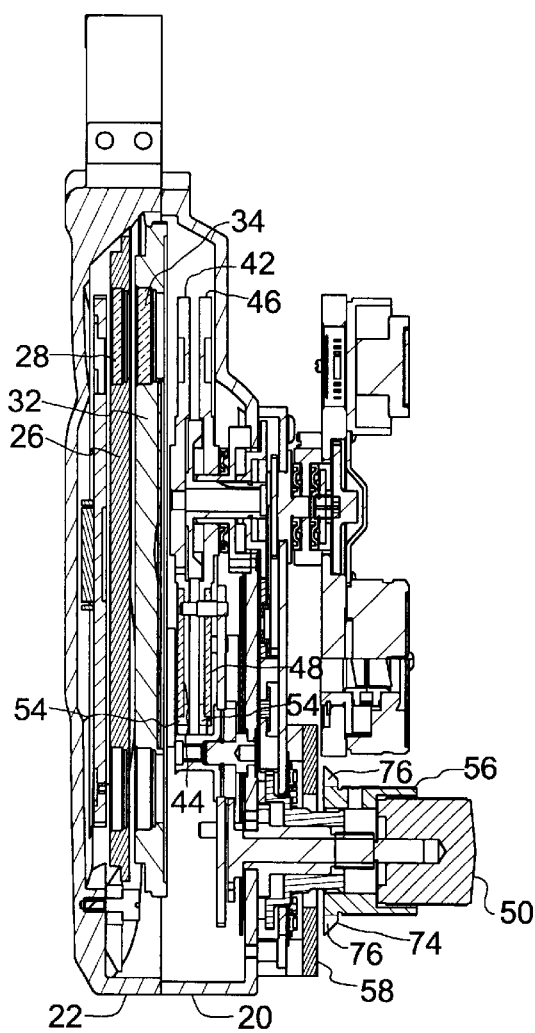
FIG. 6 is a view taken generally along the section line I—I in FIG. 3.
Figure 8:
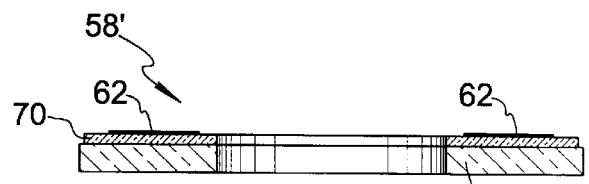
FIG. 8 is a cross-sectional view showing an alternative construction of a cylinder axis scale in accordance with the present invention.

Attention is directed now to FIGS. 5 through 7, wherein an arrangement for illuminating cylinder axis scale 58 is shown. More specifically, the cylinder axis scale 58 is formed as a light-transmitting component having opaque scale gradations 62, and a polar array of illumination sources 64 is arranged to project light through the light-transmitting cylinder axis scale. In a preferred embodiment, illumination sources 64 are light-emitting diodes on a flexible circuit board 66 installed behind cylinder axis scale 58 within a bore 61 through turret island 19. Cylinder axis scale 58 is preferably formed of a translucent material, resulting in a diffusely illuminated cylinder axis scale and substantially eliminating localized bright spots at locations corresponding to illumination sources 64. The scale gradations 62 can be printed or otherwise applied directly to the front surface of cylinder axis scale 58, and are preferably opaque for sake of contrast. In an alternative construction shown in FIG. 8, cylinder axis scale 58' is formed in two layers fixed to one another. A first layer 68 closest to illumination sources 64 is formed of a translucent material for light diffusion, and a second layer 70 is formed of a transparent material that lends itself more readily to printing or otherwise applying scale gradations 62.

Figure 9:
FIG. 9 is cross-sectional view showing another alternative construction of a cylinder axis scale in accordance with the present invention.
Figure 10:
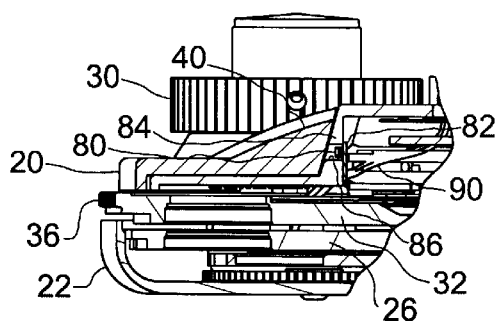
FIG. 10 is a view taken generally along the section line III—III in FIG. 4.

The present invention encompasses another alternative construction of cylinder axis scale 58" according to FIG. 9. Here, cylinder axis scale 58" is made of a photoluminescent material 72 having scale gradations 62 applied thereto. Consequently, cylinder axis scale 58 "glows in the dark," and its luminescence is recharged when the examination room lights are brightened.

While illumination of cylinder axis scale 58 as described above substantially solves the problem with respect to enabling the operator to comfortably read the cylinder axis angle, it is nevertheless desirable to also improve the visibility of cylinder axis pointers 60 on cylinder axis knob 56 in conjunction with the cylinder axis scale. Because pointers 60 are commonly provided on a beveled flange portion 74 of cylinder axis knob 56 that overlaps an inner annular region of cylinder axis scale 58, pointers 60 can be formed as light-transmitting areas 76 through flange portion 74, as shown in FIGS. 6 and 7. In a particularly simple reduction to practice, light-transmitting areas 76 are cut-out areas formed through flange portion 74. Another possible approach is to construct beveled flange portion 74 from a transparent or translucent material, and applying opaque markings as pointers 60 to the flange portion.

Figure 3:
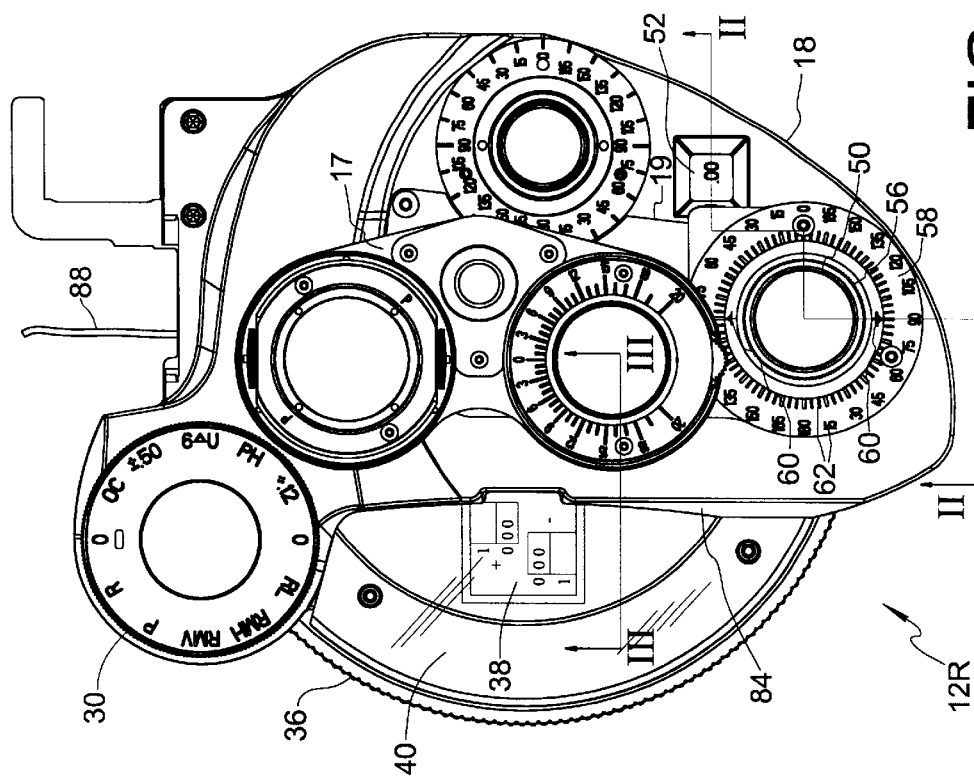
FIG. 3 is a rear elevational view of a right-eye battery of the ophthalmic refractor shown in FIGS. 1 and 2.
Figure 4:
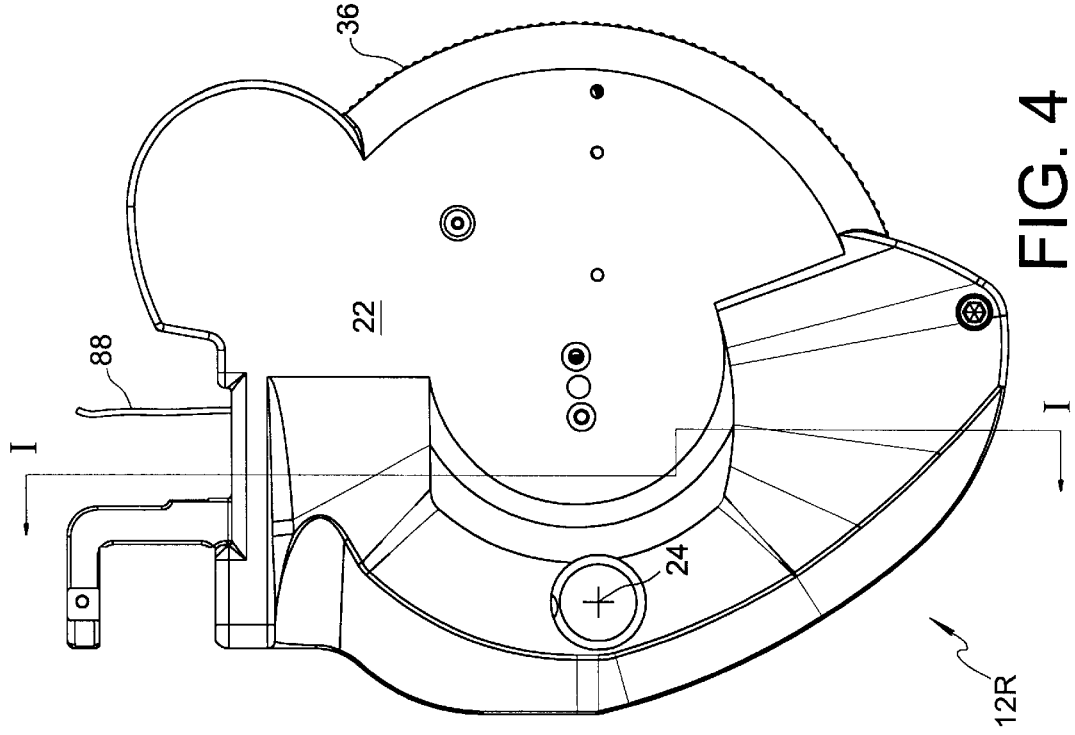
FIG. 4 is a front elevational view of the right eye-battery shown in FIG. 3.

The problem of illuminating cylinder power readout 52 is solved, according to the present invention, by providing a cylinder power illumination source 78 near cylinder power readout 52 as depicted in FIG. 7. Cylinder power illumination source 78 is independent from the array of illumination sources 64 described above, and is dedicated solely to the illumination of cylinder power readout 52. In a currently preferred construction, cylinder power illumination source 78 is a light-emitting diode and, due to the proximity of cylinder power readout 52 to cylinder axis scale 58, is provided on the same circuit board 66 that carries the polar array of illumination sources 64. Cylinder power illumination source 78 can be located along an edge of turret island 19 as shown in FIG. 3.

Similarly, at least one sphere power illumination source 80 is located near sphere power readout 38 for enhancing visibility of the readout, as can be understood with reference to FIGS. 5 and 9. FIG. 5 shows two slightly spaced illumination sources 80, however one central illumination source 80 may also be used with desired results. Illumination sources 80 are preferably light-emitting diodes on a flexible circuit board 82 fastened to the inside surface of a wall 84 of housing 18 that extends alongside sphere power readout 38 and abuts with an edge of transparent cover portion 40, with corresponding portals 86 being provided through wall 84 to allow light to reach the area of sphere power readout 38.

The circuit boards 66 and 82 are connected in series by wires 88 and 90 for connecting a power source to the various illumination diodes. In order to keep power cords out of the way of both the patient and the operator, wire 88 is preferably routed through housing 18 and central support 15 to the location where the central support is pivotally connected to mounting bracket 16. In accordance with the present invention, a slip ring 92 is provided to conduct current across the pivot junction between central support 15 and mounting bracket 16. The wiring then continues as wire 93 through mounting bracket 16 to an externally accessible female connection jack 94 on the mounting bracket which receives a male plug (not shown) from a power transformer (also not shown) connected to a wall outlet.

A major advantage of the refractor illumination scheme of the present invention is that it is well suited for application to existing ophthalmic refractors through a retrofitting procedure. During a retrofit in accordance with the present invention, cylinder power knob 50, cylinder axis knob 56, and cylinder axis scale 58 are removed from housing 18. Typically, these elements are removably attached using readily accessible set screws. Other elements, such as a cross-cylinder and prism turret 17 and turret island 19 are also removed as necessary to permit housing 18 to be opened by unscrewing fasteners that hold front half-shell 20 and rear half-shell 22 together. In preparation for sphere power illumination source 80, portal 86 is machined through the wall 86. Circuit boards 66 and 82 are then fixed in place by adhesive, screws, or other suitable means, and power lines 88 and 90 leading thereto are arranged to extend within open spaces in housing 18. A hole may be drilled through the housing to permit a connection jack to be mounted for external access, or a slip ring 92 may be installed at the mounting bracket as described above to allow less conspicuous arrangement of the wiring leading to a more remotely located connection jack. The battery housing is then closed by reattaching front half-shell 20 to rear half-shell 22.

Next, light-transmitting cylinder axis scale 58 is installed in place of the original cylinder axis scale overtop the ring of diodes 66 on circuit board 66. The original cylinder axis knob 56 can then be replaced, preferably after machining cut-out areas defining cylinder axis pointers 60. As an alternative, a new pre-fabricated cylinder axis knob can be installed that already has cut-out areas defining pointers 60, or that has a translucent flange portion 74 with opaque pointer markings. The original cylinder power knob 50 is reinstalled to complete reassembly.

As will be appreciated from the foregoing description, the improvement and method of the present invention provide reliable and effective illumination of the cylinder axis scale, cylinder power readout, and sphere power readout of a conventional ophthalmic refractor using commercially available components. The invention is applicable to original equipment to help new purchasers, and through retrofit to help existing ophthalmic refractor users.

What is claimed is:

1. In an ophthalmic refractor of the type having a cylinder power knob for selectively positioning at least one cylinder lens of chosen power in a patient viewing path of said ophthalmic refractor; a cylinder power readout corresponding to said cylinder power knob for displaying the resultant power of said at least one cylinder lens to an operator; a polar cylinder axis scale; and a cylinder axis knob coaxial with and rotatable relative to said cylinder axis scale for adjusting the cylinder axis of said at least one cylinder lens, said cylinder axis knob including a cylinder axis pointer cooperating with said cylinder axis scale for indicating said cylinder axis to an operator; the improvement comprising:

said cylinder axis scale being formed as a light-transmitting component having opaque scale gradations;

a polar array of light-emitting diodes mounted on a single circuit board and arranged to project light through said cylinder axis scale; and means for connecting a power source to said circuit board, said power source being external to said ophthalmic refractor.

2. The improvement according to claim 1, wherein said cylinder axis pointer is formed as a light-transmitting area on said cylinder axis knob that overlaps with said cylinder axis scale.

3. The improvement according to claim 2, wherein said light-transmitting area is a cut-out area.

4. The improvement according to claim 1, wherein said cylinder axis scale comprises a first layer of a translucent material adjacent said polar array of illumination sources and a second layer of a transparent material over said first layer, said second layer having said opaque scale gradations applied thereto.

5. The improvement according to claim 1, wherein said cylinder axis scale is formed of a translucent material having said opaque scale gradations applied thereto.

6. The improvement according to claim 1, further comprising a cylinder power illumination source mounted on said single circuit board and located near said cylinder power readout.

7. The improvement according to claim 1, wherein said ophthalmic refractor additionally has a strong sphere control knob for selectively positioning a strong sphere lens of chosen power in said patient viewing path, a weak sphere control dial for selectively positioning a weak sphere lens of chosen power in said patient viewing path, and a sphere power readout for displaying the cumulative power of said chosen strong and weak sphere lenses to an operator, and said improvement further comprises:

a sphere power illumination source located near said sphere power readout; and means for connecting said power source to said sphere power illumination source.

8. The improvement according to claim 1, wherein said ophthalmic refractor is of the type having a mounting bracket pivotally connected thereto, and said means for connecting a power source comprises a slip ring for conducting electricity through said pivotal connection of said mounting bracket.

9. In an ophthalmic refractor of the type having a cylinder power knob for selectively positioning at least one cylinder lens of chosen power in a patient viewing path of said ophthalmic refractor; a cylinder power readout corresponding to said cylinder power knob for displaying the resultant power of said cylinder lens to an operator; a polar cylinder axis scale; and a cylinder axis knob coaxial with and rotatable relative to said cylinder axis scale for adjusting the cylinder axis of said at least one cylinder lens, said cylinder axis knob including a cylinder axis pointer cooperating with said cylinder axis scale for indicating said cylinder axis to an operator; the improvement comprising:

said cylinder axis scale including a photoluminescent material having scale gradations applied thereto.

10. The improvement according to claim 9, wherein said cylinder axis pointer is formed as a light-transmitting area on said cylinder axis knob that overlaps with said cylinder axis scale.

11. The improvement according to claim 10, wherein said light-transmitting area is a cut-out area.

12. The improvement according to claim 9, further comprising a cylinder power illumination source located near said cylinder power readout, and means for connecting a power source to said cylinder power illumination source, said power source being external to said ophthalmic refractor.

13. The improvement according to claim 12, wherein said ophthalmic refractor is of the type having a mounting bracket pivotally connected thereto, and said means for connecting a power source comprises a slip ring for conducting electricity through said pivotal connection of said mounting bracket.

14. The improvement according to claim 9, wherein said ophthalmic refractor additionally has a strong sphere control knob for selectively positioning a strong sphere lens of chosen power in said patient viewing path, a weak sphere control dial for selectively positioning a weak sphere lens of chosen power in said patient viewing path, and a sphere power readout for displaying the cumulative power of said chosen strong and weak sphere lenses to an operator, and said improvement further comprises:

a sphere power illumination source located near said sphere power readout; and means for connecting a power source to said sphere power illumination source, said power source being external to said ophthalmic refractor.

15. The improvement according to claim 14, wherein said ophthalmic refractor is of the type having a mounting bracket pivotally connected thereto, and said means for connecting a power source comprises a slip ring for conducting electric current through said pivotal connection of said mounting bracket.

16. A method for retrofitting an ophthalmic refractor of the type having a left-eye battery housing and a right-eye battery housing, each said battery housing having mounted thereon a cylinder power knob for selectively positioning at least one cylinder lens of chosen power in a patient viewing path of said ophthalmic refractor; a cylinder power readout corresponding to said cylinder power knob for displaying the resultant power of said at least one cylinder lens to an operator; a polar cylinder axis scale; and a cylinder axis knob coaxial with and rotatable relative to said cylinder axis scale for adjusting the cylinder axis of said at least one cylinder lens, said cylinder axis knob including a cylinder axis pointer cooperating with said cylinder axis scale for indicating said cylinder axis to an operator; said method comprising the steps of:

A) removing said cylinder axis knob and said cylinder axis scale from each said battery housing;

B) opening each said battery housing;

C) fixing a polar array of illumination sources within each said battery housing;

D) arranging power lines leading to each said polar array of illumination sources for enabling a power source to be connected thereto;

E) closing each said battery housing;

F) installing a replacement cylinder axis scale over each said polar array of illumination sources, said replacement cylinder axis scale being formed as a light-transmitting component having opaque scale gradations; and G) mounting a specified cylinder axis knob to be coaxial with each said replacement cylinder axis scale.

17. The method according to claim 16, wherein said specified cylinder axis knob is the same cylinder axis knob removed in step (A).

18. The method according to claim 16, further comprising the step of machining a cut-out area in place of said cylinder axis pointer.

19. The method according to claim 16, wherein said specified cylinder axis knob is a different cylinder axis knob from the cylinder axis knob removed in step (A).

20. The method according to claim 19, wherein said different cylinder axis knob has a cylinder axis pointer formed as a light-transmitting area on said different cylinder axis knob.

21. The method according to claim 16, further comprising the step of installing a cylinder power illumination source in each said battery housing proximate said cylinder power readout thereof.

22. The method according to claim 16, further comprising the steps of providing a portal through each said battery housing near said sphere power readout thereof, and installing a sphere power illumination source adjacent said portal to illuminate said sphere power readout.

* * * * *